(12) United States Patent
Irving et al.

(10) Patent No.: US 8,197,622 B2
(45) Date of Patent: Jun. 12, 2012

(54) SYSTEM AND METHOD FOR DETECTING FEATURES ON A LAMINATED VENEER LUMBER BILLET

(75) Inventors: David C. Irving, Boise, ID (US); Thomas J. Taylor, Seattle, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 438 days.

(21) Appl. No.: 12/622,608

(22) Filed: Nov. 20, 2009

(65) Prior Publication Data

US 2011/0120618 A1 May 26, 2011

(51) Int. Cl.
*G06T 7/00* (2006.01)
(52) U.S. Cl. .......... 156/64; 156/378; 156/379; 264/406; 264/407; 264/408
(58) Field of Classification Search .................... 156/64, 156/378, 379; 264/406, 407, 408
See application file for complete search history.

(56) References Cited

U.S. PATENT DOCUMENTS

| | | | |
|---|---|---|---|
| 5,421,951 A | 6/1995 | Troutner et al. | |
| 5,652,065 A | 7/1997 | Park et al. | |
| 5,960,104 A * | 9/1999 | Conners et al. | 382/141 |
| 6,056,841 A | 5/2000 | Knokey | |
| 6,594,590 B2 | 7/2003 | Woods et al. | |
| 6,652,789 B1 | 11/2003 | Pearson | |
| 2004/0195714 A1 * | 10/2004 | Mbachu et al. | 264/40.1 |

OTHER PUBLICATIONS

Bucur, Voichita, Ultrasonic and X-Ray Techniques for Nondestructive Evaluation of Wood, posted to world-wide web Jun. 26, 2002 at http://www.sea-acustica.es/Sevilla02/ult03002.pdf, Univesite Henri Poincare, Nancy I, Faculte Sciences et Techniques Biologiques, Laboratoire d'Essais et Recherches sur le Materiau Bois, BP 239, 54506, Vandoeuvre les Nancy, France.

* cited by examiner

*Primary Examiner* — Katarzyna Wyrozebski Lee
*Assistant Examiner* — Joshel Rivera
(74) *Attorney, Agent, or Firm* — Weyerhaeuser Law Dept (57) ABSTRACT

The disclosure relates to systems and methods for detecting features on billets of laminated veneer lumber (LVL). In some embodiments, an LVL billet is provided and passed through a scanning assembly. The scanning assembly includes an x-ray generator and an x-ray detector. The x-ray generator generates a beam of x-ray radiation and the x-ray detector measures intensity of the beam of x-ray radiation after is passes through the LVL billet. The measured intensity is then processed to create an image. Images taken according to the disclosure may then be analyzed to detect features on the LVL billet.

7 Claims, 10 Drawing Sheets

SYSTEM AND METHOD FOR DETECTING FEATURES ON A LAMINATED VENEER LUMBER BILLET

TECHNICAL FIELD

The present disclosure is directed generally to systems and methods for detecting features on laminated veneer lumber (LVL). More specifically the disclosure is directed to detecting the presence of slips sheets on LVL and determining the lengths of lap joints on LVL.

BACKGROUND

Laminated veneer lumber (LVL) is an engineered wood product that is fabricated from sheets of thin wood pieces (e.g., veneers) that are glued together in panels called billets. When LVL is manufactured, the veneers are oriented so that the grain in each individual sheet is aligned primarily along the length of the billet. Pieces of LVL are trimmed from the billet for use in a variety of applications (e.g., joists, headers, beams, rafters, flanges for I-joists, etc.).

Figure 1:
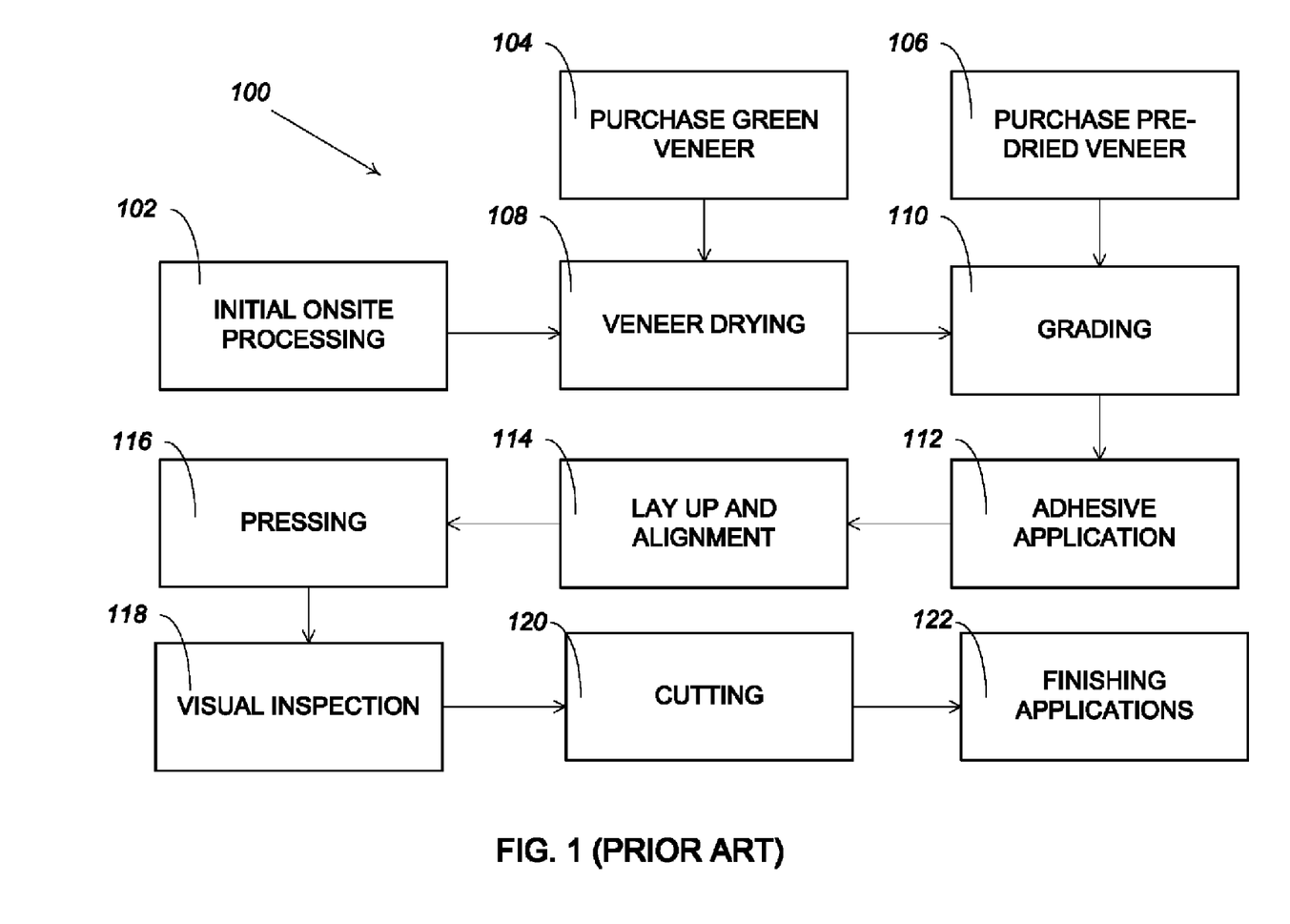
FIG. 1 is a flow chart depicting a conventional LVL manufacturing process.

FIG. 1 is a flow chart depicting a conventional LVL manufacturing process 100. The start of the LVL manufacturing process 100 depends on how the plant running the process 100 obtains the veneers. Plants may either peel and dry veneers onsite (step 102), purchase green veneers (step 104) and dry them onsite (step 108), or purchase pre-dried veneers (step 106).

After initial processing, the veneers are graded for stiffness and/or strength as shown in step 110. Generally, veneer grading is a highly automated process involving both visual grading methods and automatic grading methods (e.g., ultrasonics). The objective of grading is to permit the most efficient use of the available veneer. The lower grade veneers are used for the LVL core and the higher grade veneers are used in the LVL face.

Figures 2, 3:
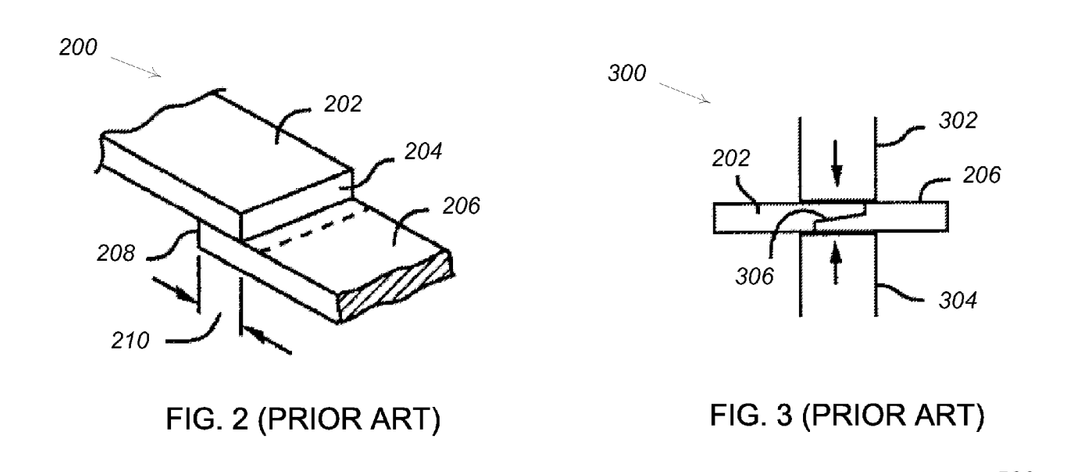
FIG. 2 is a perspective view of a veneer alignment step according to the method described in FIG. 1.
FIG. 3 is a side view of the veneer being pressed according to the method described in FIG. 1.

Following grading, the veneers are laid out and prepared for pressing. An adhesive (e.g., a resin) is applied to the veneers (step 112) and the veneers are aligned or laid up (step 114). FIG. 2 shows a typical veneer lay up 200 according to the method described in FIG. 1. As shown in FIG. 2, a first veneer piece 202 having a first edge 204 is aligned next to a second veneer piece 206 having a second edge 208 so that the first edge 204 and the second edge 208 overlap. The overlapping distance is shown as reference character 210. LVL billets are produced by applying layers of veneer and adhesive sequentially. Some plants utilize modular assembly systems containing a station for each successive layer of veneer in the product.

After lay up, the veneers are pressed. During pressing (step 116), LVL is manufactured to either a fixed length using a batch press, or to an indefinite length using a continuous press. FIG. 3 shows an example of a pressing operation 300. In FIG. 3, the veneers and placed between a first platen 302 and a second platen 304. The first platen 302 and second platen 304 are pressed toward each other to form a lap joint 306. The presses are heated by electricity, microwaves, hot oil, steam, or radio-frequency (RF) waves. Press temperatures range from about 120° to 230° C. (250° to 450° F.). The exact pressing conditions are designed to bring the veneer surfaces tightly together without over-compressing the wood.

Figure 4:
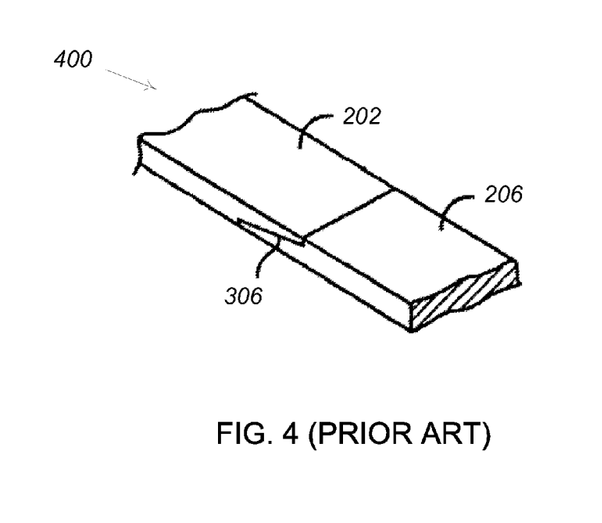
FIG. 4 is a perspective view of a lap joint on a finished billet after it is removed from the press according to the method described in FIG. 1.

FIG. 4 shows the lap joint 306 in a finished billet 400 after it is removed from the press. Billets exiting the press may be up to 8.9 centimeters (3.5 inches) thick. Billets are produced in widths of up to 2.8 meters (4 feet). After exiting the press, the billets are visually inspected (step 118) to identify particular features (e.g., lap lengths, slip sheets).

After inspection, the billets are cut into LVL (step 120). The billets are typically cut into numerous strips based on customer specifications. The LVL is produced in lengths up to the maximum shipping length of 24 meters (80 ft). After the LVL is cut, other finishing applications may be performed (e.g., sorting, treating, stacking, stamping) as depicted by step 122.

Figure 5:
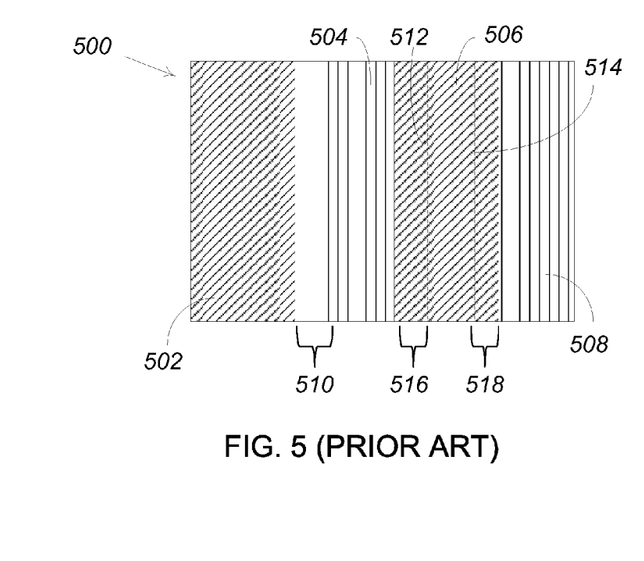
FIG. 5 is a top view of a finished billet.

A common challenge in veneer manufacturing is avoiding the formation of slip sheets. A slip sheet is a feature where two pieces of veneer intended to form a lap joint have failed to overlap. FIG. 5 is a top view of a billet 500 which illustrates this problem. The portion of the billet 500 shown is formed by a first veneer sheet 502, a second veneer sheet 504, a third veneer sheet 506, and a fourth veneer sheet 508. The first veneer sheet 502 and the second veneer sheet 504 have failed to overlap, forming a slip sheet depicted as reference character 510. In contrast the second veneer sheet 504 has been pressed to adhere to the third veneer sheet 506, forming a lap joint shown as a dotted line 512. Likewise, the third veneer sheet 506 has adhered to the fourth veneer sheet 508 forming a lap joint shown as a dotted line 514. Features such as the slip sheet 510 may cause the potion of the billet 500 where the veneer sheets do not properly overlap to exhibit inferior mechanical properties when compared with the portions of the billet 500 where proper lap joints have been formed. Currently slip sheets and other features are detected visually by workers who inspect the billets for visible defects (see step 120 in FIG. 1). Therefore, there is an opportunity to improve LVL manufacturing processes by developing automated methods for inspection.

In addition to avoiding slip sheet formation, LVL manufacturers also strive to optimize the length of the lap joints which are successfully created. The length of a lap joint is commonly referred to as a lap length. Lap length is currently determined visually during the inspection step 120 from FIG. 1. Lap lengths that are too short may result in the manufacture of final product that has inferior mechanical properties. On the other hand, manufacturing LVL with a lap length that is too long is not an efficient use of the raw materials in supply. Currently presses are without any direct feedback or indication of lap position. Therefore, it is common practice to operate with excessive laps to reduce the risk of product fall down.

Thus, there is a need to develop improved systems and methods for detecting features during LVL manufacturing. Specifically, there is a need to develop systems and methods for detecting lap lengths and slip sheets in billets. Such systems and methods could be used to optimize the LVL manufacturing process and to control the quality of the final product.

SUMMARY

The following summary is provided for the benefit of the reader only and is not intended to limit in any way the invention as set forth by the claims. The present disclosure is directed generally towards to systems and methods for detecting features on laminated veneer lumber.

In some embodiments, the system includes a frame, a scanning assembly, and an image processor. The scanning assembly includes an x-ray generator and an x-ray detector. The x-ray generator generates a beam of x-ray radiation and the x-ray detector measures intensity of the beam of x-ray radiation after is passes through the LVL billet. The measured intensity is then processed to create an image. Images taken according to the disclosure may then be analyzed to detect features on the LVL billet.

BRIEF DESCRIPTION OF THE DRAWINGS

The present disclosure is better understood by reading the following description of non-limitative embodiments with reference to the attached drawings wherein like parts of each of the figures are identified by the same reference characters, and are briefly described as follows.

The present disclosure describes generally to systems and method for detecting features (e.g., slip sheets, lap lengths) on laminated veneer lumber. Certain specific details are set forth in the following description and FIGS. 6-13 to provide a thorough understanding of various embodiments of the disclosure. Well-known structures, systems, and methods often associated with such systems have not been shown or described in details to avoid unnecessarily obscuring the description of various embodiments of the disclosure. In addition, those of ordinary skill in the relevant art will understand that additional embodiments of the disclosure may be practiced without several of the details described below.

In this disclosure, the term "wood" is used to refer to any cellulose-based material produced from trees, shrubs, bushes, grasses or the like. The disclosure is not intended to be limited to a particular species or type of wood. The term "laminated veneer lumber" (LVL) is used to refer to engineered wood product that uses multiple layers of thin wood pieces (e.g., veneers) assembled with adhesives. The term "billet" is used to refer to a semi-finished LVL product. The term "lap joint" is used to refer to a joint formed when one piece of veneer is placed partly over another and bonded. The term "lap length" is used to refer to the length of a lap joint. The term "slip sheet" is used to refer to a feature encountered in LVL manufacturing in which two pieces of veneer intended to form a lap joint have failed to overlap.

Figure 6:
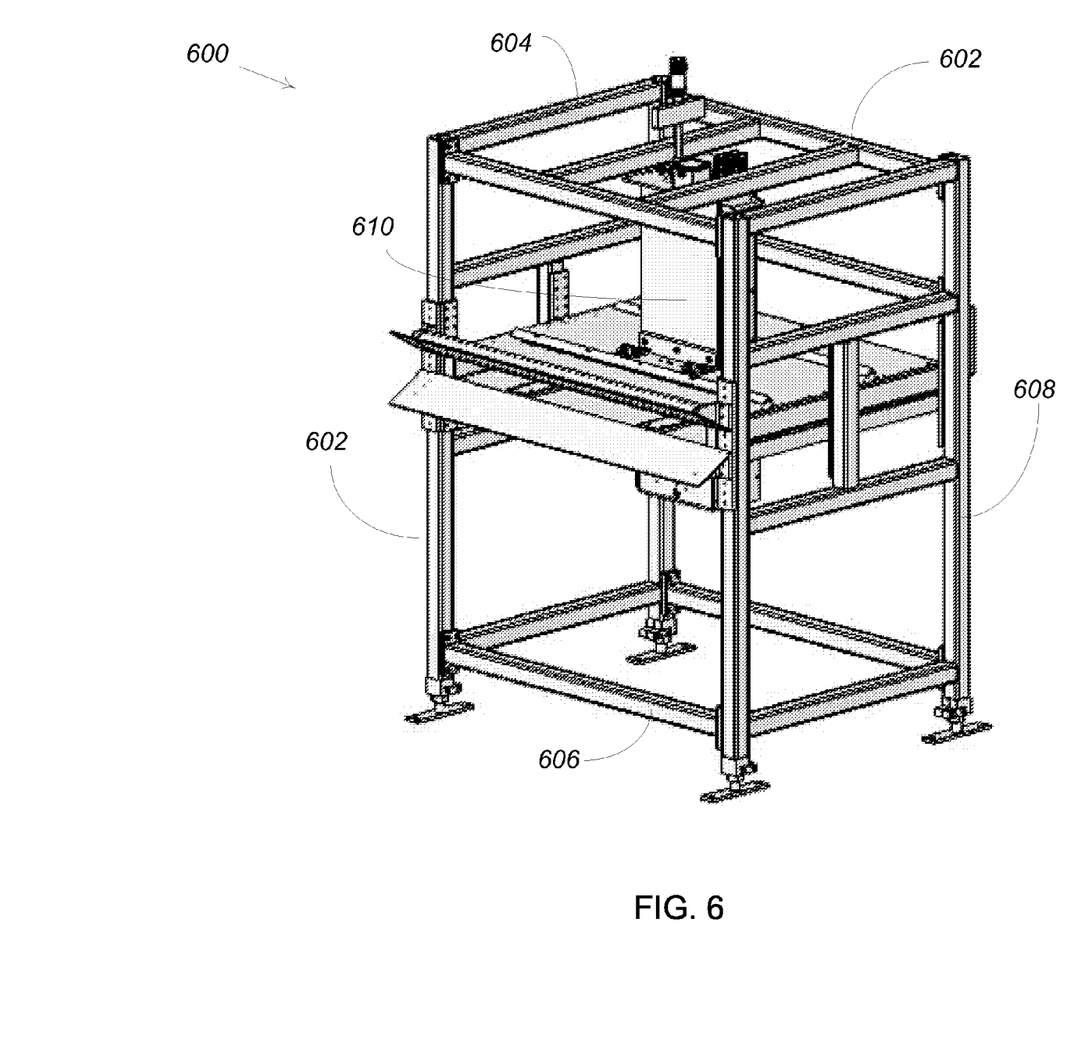
FIG. 6 is an isometric view of a system for detecting features on a billet according to embodiments of the disclosure.
Figure 7:
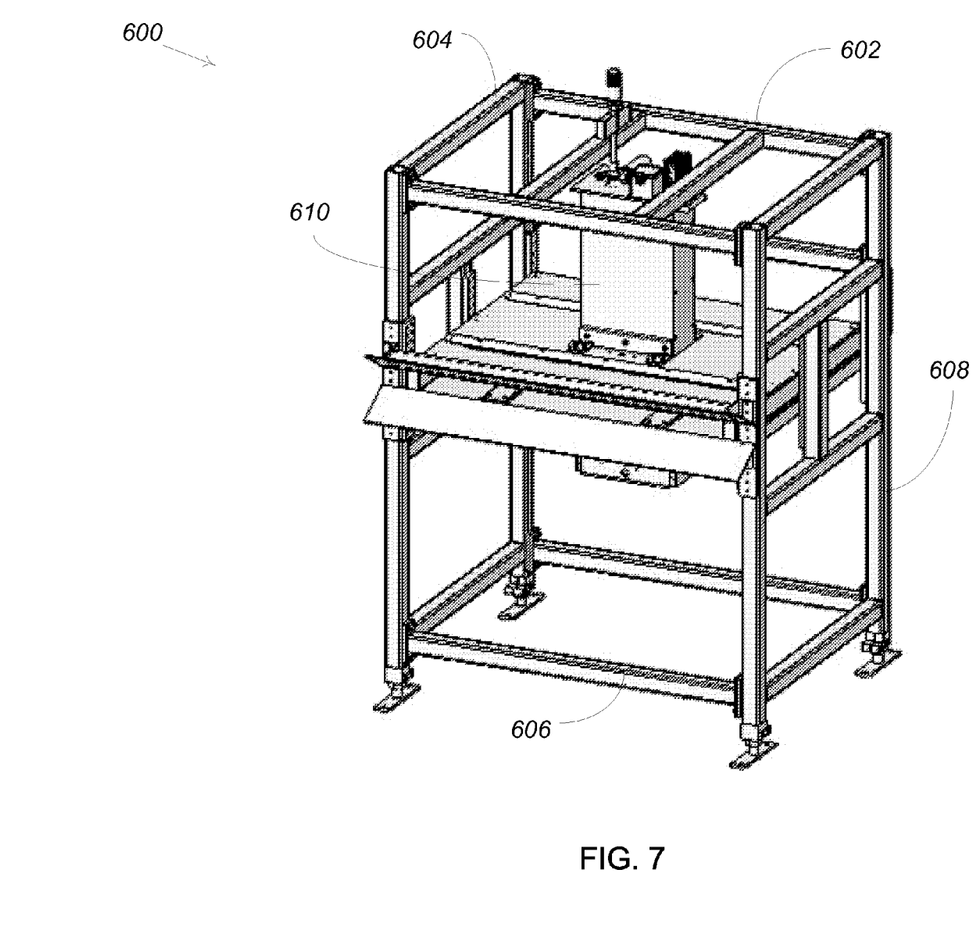
FIG. 7 is another isometric view of a system for detecting features on a billet according to embodiments of the disclosure.

FIGS. 6 and 7 are isometric views of a system 600 for detecting features in an LVL billet according to embodiments of the disclosure. The system 600 may include a frame 602 to support equipment for scanning the billet to detect features. In some embodiments, the frame 602 includes upper components 604, lower components 606, and side components 608.

In the embodiment shown, the upper components 604 are arranged in a substantially parallel configuration. The lower components 606 are located a distance from the upper components 604. The lower components 606 are also arranged in a substantially parallel configuration. The side components 608 connect the upper components 604 to the lower components 606. The frame 602 can be constructed from any conventional material known to those of ordinary skill in the art. Additionally, the components of the frame 602 may be arranged in other configurations that are different from the specific configuration shown in FIGS. 6 and 7.

Figure 8:
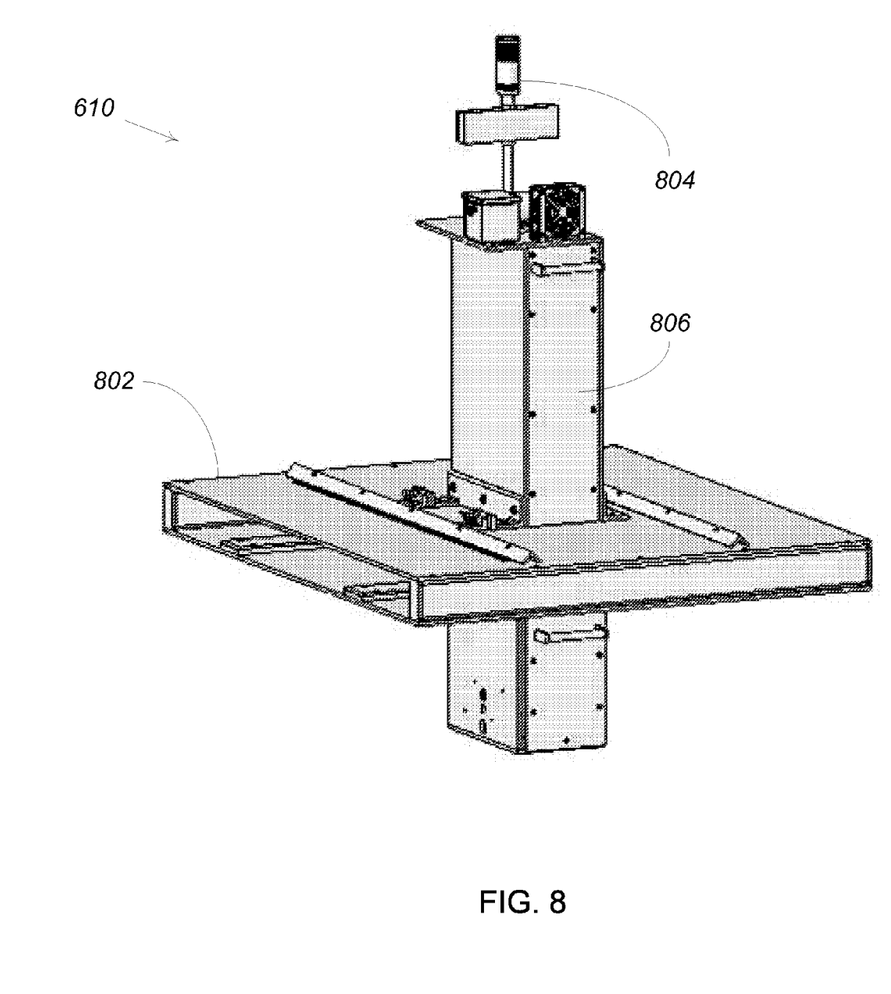
FIG. 8 is an isometric view of a scanning assembly according to embodiments of the disclosure.

The frame 602 supports a scanning assembly 610. An embodiment of the scanning assembly 610 is shown in more detail in FIG. 8. The scanning assembly 610 may include a platform 802 for receiving an LVL billet (not shown in FIG. 8) for scanning. An x-ray generator 804 may be positioned above the platform 802 so that a beam of radiation generated by the x-ray generator 804 is directed toward a first planar surface on the LVL billet when the LVL billet placed on the platform 802. In the embodiment shown, the x-ray generator 804 is an x-ray tube; however, radioactive isotope sources of x-ray radiation may also be used. The scanning assembly 610 may further include a collimator 806 which serves to narrow the beam generated by the x-ray generator 806. In FIG. 8, the collimator 806 is shown as a box extending through the platform 802. An x-ray detector (not visible in FIG. 8) is positioned inside the box on the side of the platform 802 opposite the x-ray generator 804.

Figure 9:
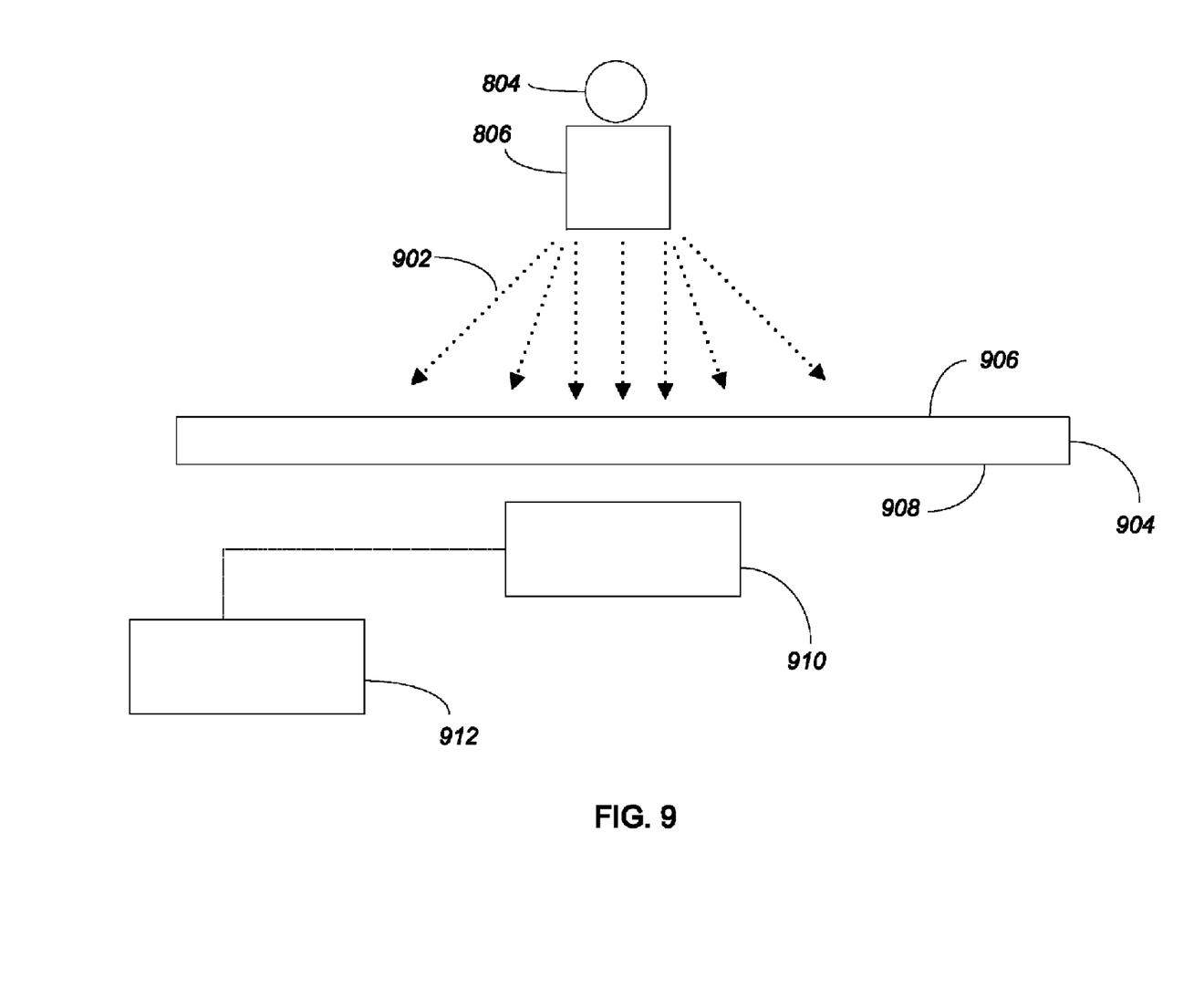
FIG. 9 is a schematic illustrating the operation of the scanning assembly according to embodiments of the disclosure.

FIG. 9 is a schematic which illustrates the operation of the scanning assembly 610 according to embodiments of the disclosure. Referring to FIG. 9, the x-ray generator 804 generates a beam of radiation (shown as dotted lines 902) which is narrowed and directed by the collimator 806. The beam 902 is projected toward a billet 904 having a first planar surface 906 and a second planar surface 908. An x-ray detector 910 is positioned below the billet 904 to measure the intensity of the beam 902 after passing through the billet 904. In some embodiments, the x-ray detector 910 may be a linear array detector or any other device that is suitable for the purpose of x-ray detection known to one of ordinary skill in the art. The x-ray detector 910 is connected to an image processor 912 (e.g., any standard computer suitable for such use), which generates an image based on the intensity measured by the x-ray detector 910.

The generated image represents a measurement of the absolute density of the billet 904 across its length. According to embodiments of the disclosure, the image may be analyzed to detect features (e.g. lap lengths, slip sheets). The image generated may be comprised of one or more pixels arranged in one or more columns. In some embodiments, the entire image is used to identify features; in other embodiments, the image may be cropped and the analysis based on only a portion of the image.

According to embodiments of the disclosure, the first step for the detecting features on the billet 904 includes calculating the mean intensity of the one or more columns to create a one-dimensional array along the length of the billet 904. The next step includes fitting a second order polynomial to the one dimensional array. To correct for background noise, the second order polynomial may then be subtracted from the one-dimensional array to create a difference array. The next step may involve passing the difference array through a low pass filter to create a filtered array. In some embodiments, a fourth order Butterworth filter having a cutoff frequency that is one tenth of the sample resolution (the rate at which images are captured) may be used for this step. The final step involves performing a peak and valley search on the filtered array to identify overlaps or gaps on the billet 904. Overlaps may be used to identify and measure lap length. Gaps may be used to identify and measure slip sheets. Since the x-ray beam is purposely oriented parallel to the overlap features of the billet, the lap features are accentuated and easily distinguished from normal background billet density variation.

Figure 10:
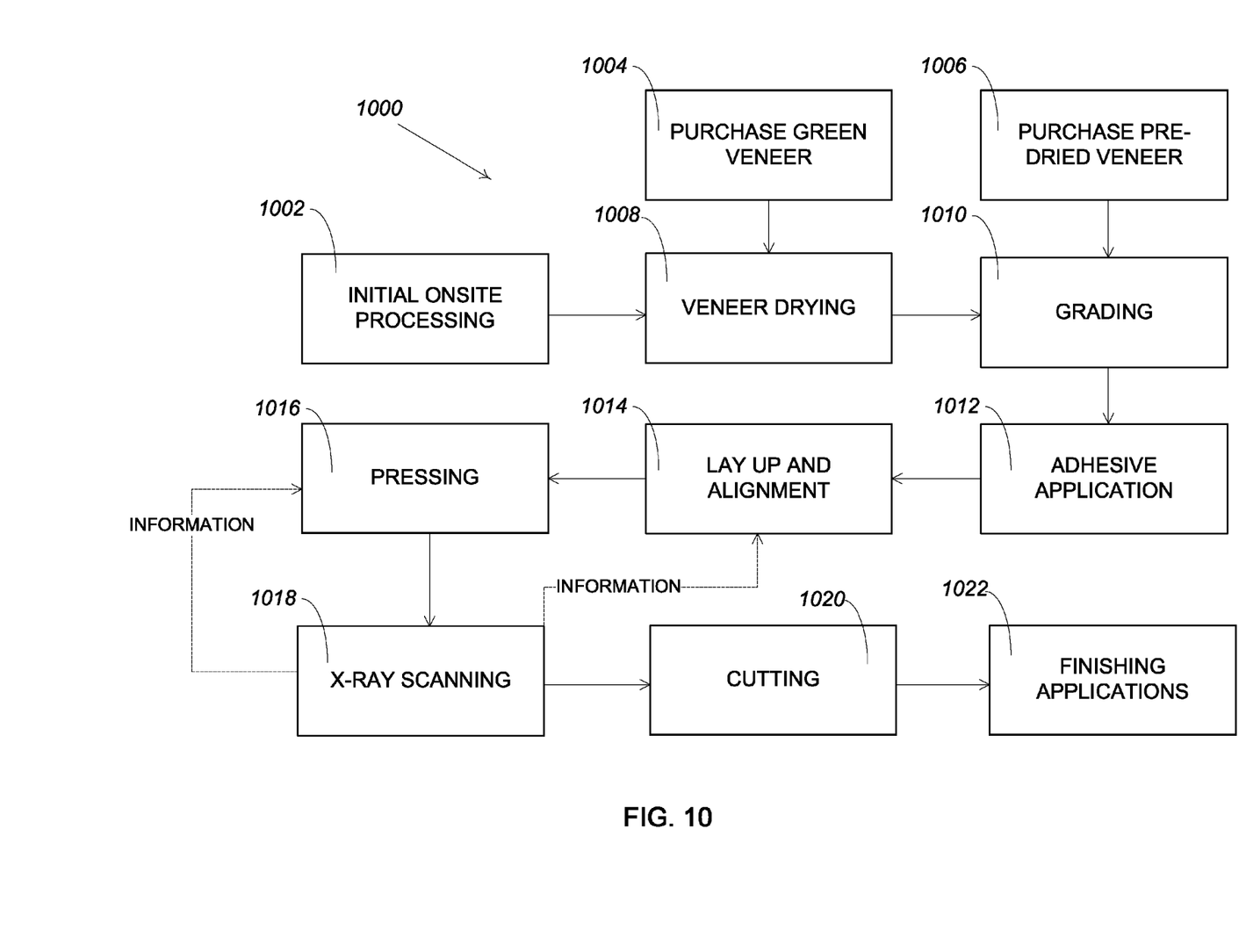
FIG. 10 is a flow chart depicting methods for manufacturing LVL according to embodiments of the disclosure.

In operation, systems and methods according to the disclosure may be used (1) as a method of quality control to eliminate products with slip sheets; or (2) to provide feedback to optimize LVL manufacturing. FIG. 10 is a flow chart depicting methods for detecting features in an LVL billet according to embodiments of the disclosure. According to FIG. 10, veneers are either peeled and dried onsite (step 1002), green veneers are purchased (step 1004) and dried onsite (step 1008), or pre-dried veneers are purchased (step 1006). The veneers are then graded according to conventional processes (step 1010) and laid out and prepared for pressing.

In embodiments related to quality control, the process resembles conventional LVL manufacturing to some degree. An adhesive is applied to the veneers (step 1012) and the veneers are aligned or laid up (step 1014). The veneers are then pressed into a billet (step 1016) using any type of pressing technology known to those of ordinary skill in the art. In embodiments according to the disclosure, a system for detecting features in an LVL billet (e.g., as shown in FIGS. 6 and 7) may be arranged at the outfeed of the press to receive the billet and scan it using methods described in the disclosure. The information obtained from the scanning may then be used to detect slip sheets on billets and remove billets having too many slip sheets or slip sheets whose size exceeds a threshold value. The billets not removed may then by cut (step 1020) and further processed (step 1022) according to conventional methods.

In embodiments related to optimizing LVL manufacturing, the information obtained from scanning may be used to detect slip joints and lap lengths and change the LVL manufacturing process to affect the production of these features. For example, the information may be fed back to step 1016 to optimize pressing cycles. Alternatively, the information may be fed back to step 1014 to alter veneer alignment. This scope of this disclosure is intended to include other methods of optimizing LVL manufacturing using the scanning information that may be apparent to those of ordinary skill in the art.

From the foregoing, it will be appreciated that the specific embodiments of the disclosure have been described herein for purposes of illustration, but that various modifications may be made without deviating from the disclosure. For example, some non-essential steps may be eliminated from the procedure described for image analysis. Aspects of the disclosure described in the context of particular embodiments may be combined or eliminated in other embodiments. For example, aspects related to embodiments associated with quality control may be combined with those associated with optimization of LVL manufacturing.

Further, while advantages associated with certain embodiments of the disclosure may have been described in the context of those embodiments, other embodiments may also exhibit such advantages, and not all embodiments need necessarily exhibit such advantages to fall within the scope of the disclosure. Accordingly, the invention is not limited except as by the appended claims.

The following example will serve to illustrate aspects of the present disclosure. The example is intended only as a means of illustration and should not be construed to limit the scope of the disclosure in any way. Those skilled in the art will recognize many variations that may be made without departing from the spirit of the disclosure.

EXAMPLE

Thirty-eight specimens of LVL billets were tested using systems and method according to the disclosure for detecting features. Each of the thirty-eight billets was manufactured using standard LVL processes and materials. The length of each billet was approximately 10 feet.

A system having a scanning assembly similar to the one shown in FIG. 8 was constructed and calibrated to measure absolute density. Each billet was passed through the scanning assembly and high resolution image was captured. For this specific test, each image captured was 128 pixels wide (e.g., a 128 pixel scan line). The billets were scanned at a lengthwise resolution of 0.100 inches.

The images were then analyzed according to methods described in this disclosure. A mean value was determined for each 128 pixel scan to create a one-dimensional array. A second order polynomial was then fit to the one dimensional array. The second order polynomial may then be subtracted from the one-dimensional array to create a difference array. The difference array was passed through a low pass filter to create a filtered array. Finally, a peak and valley search was performed on the filtered array to identify overlaps or gaps.

Figure 11:
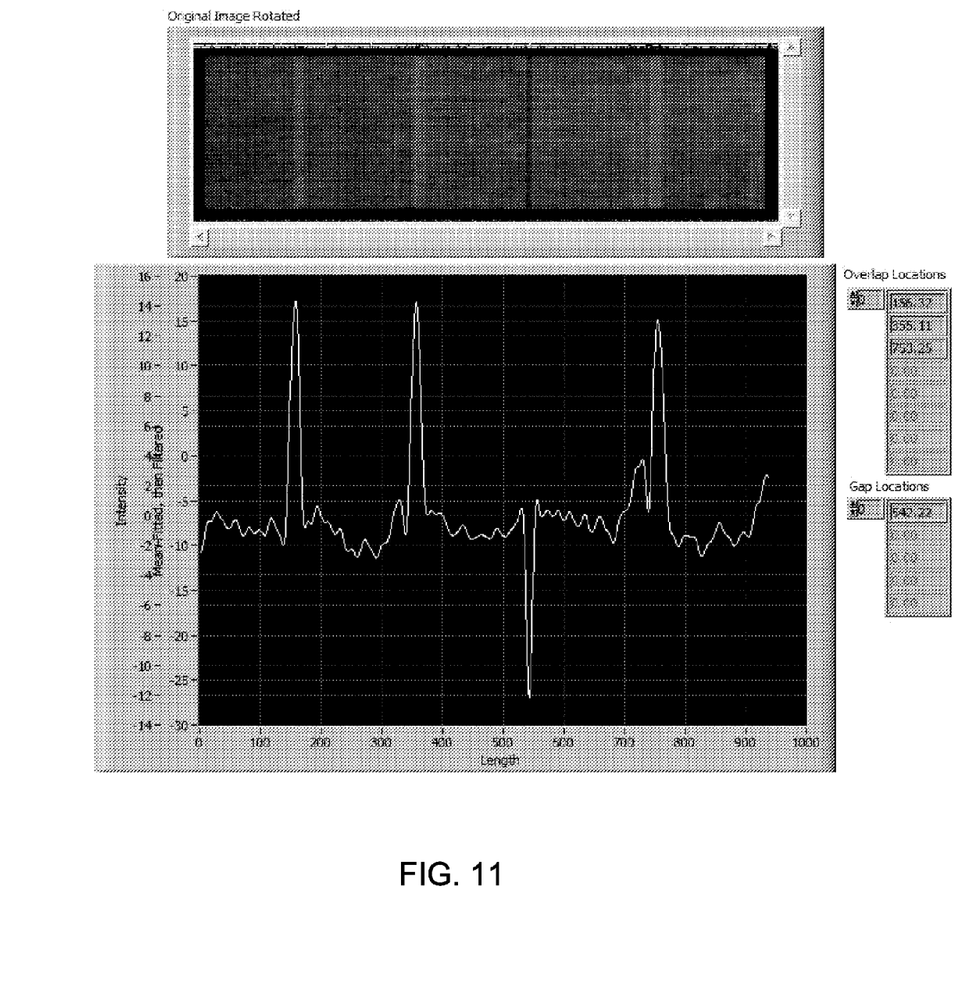
FIGS. 11-13 show images of billets taken according to embodiments of the disclosure alongside plots of intensity vs. length of the billets.
Figure 12:
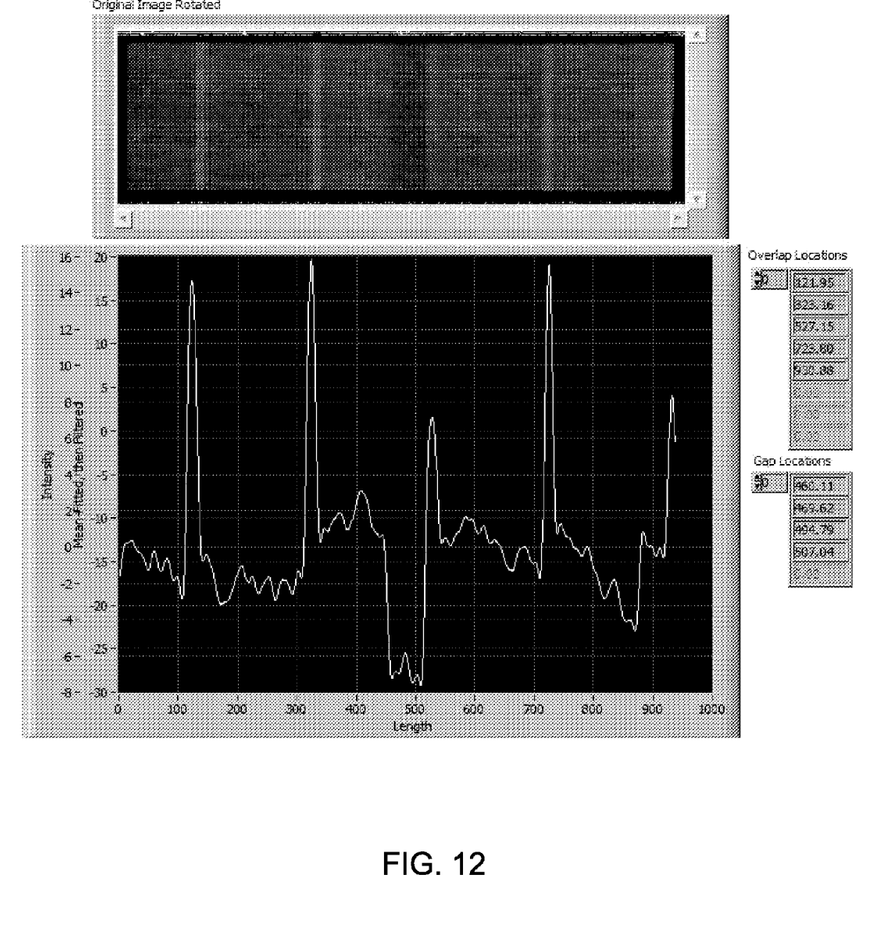
Figure 13:
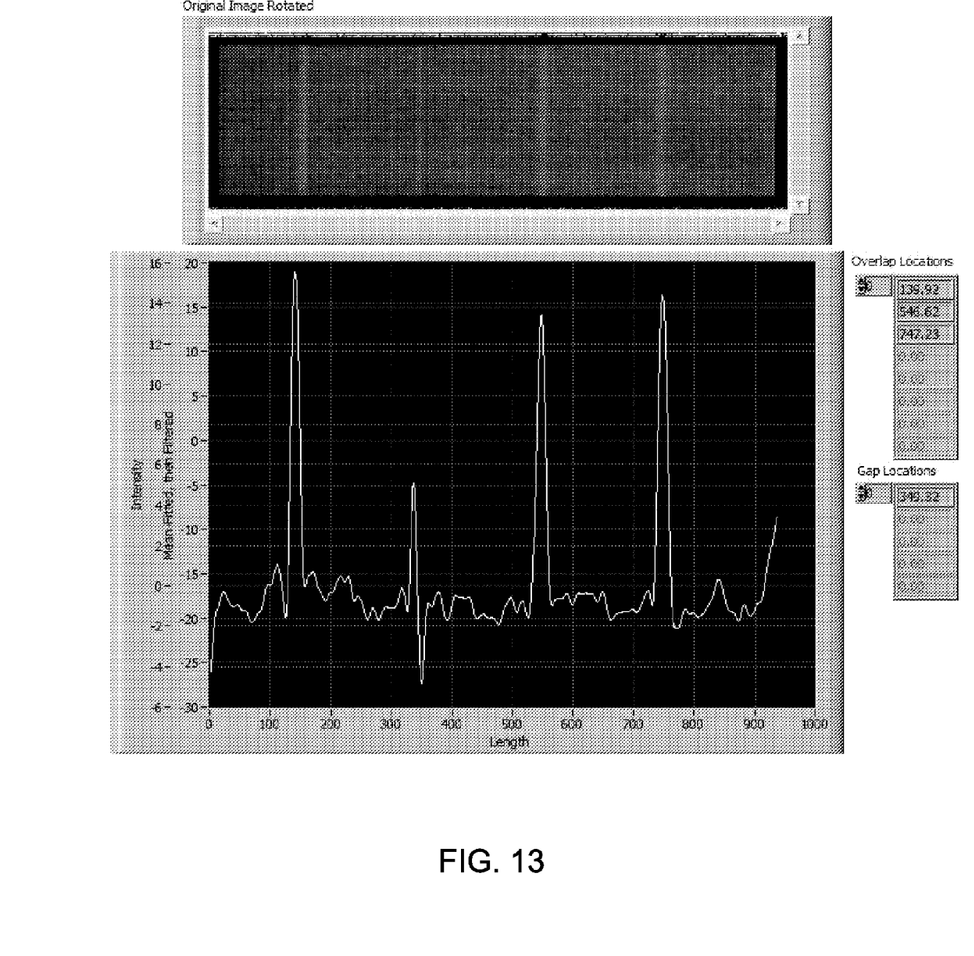

FIGS. 11-13 show images of billets taken according to embodiments of the disclosure alongside plots of intensity vs. length of the billets. Comparing the image to the plot clearly demonstrates that the peak and valley search is effective to detect features on the billets tested. For example, in FIG. 11, methods according to the disclosure correctly identified three overlap locations and one gap locations. This information may then be used to measure and identify slip sheets and lap lengths as described above.

We claim:

1. A method for detecting features on laminated veneer lumber (LVL) comprising:
   providing a billet having a first planar surface and a second planar surface;
   generating a beam of x-ray radiation onto the first planar surface;
   measuring intensity of the beam of x-ray radiation below the second planar surface after is passes through the LVL billet;
   processing the measured intensity to create an image, the image comprising one or more pixels arranged in one or more columns;
   measuring a mean intensity for each of the one or more of columns to create a one dimensional array;
   fitting a second order polynomial to the one dimensional array;
   subtracting the second order polynomial from the one-dimensional array to create a difference array;
   passing the difference array through a low pass filter to create a filtered array;
   performing a peak and valley search on the filtered array to identify features on the first billet.

2. The method of claim 1 wherein the features are substantially perpendicular to the beam of x-ray radiation.

3. The system of claim 1 wherein the features are selected from the group consisting of lap lengths or slip sheets.

4. The method of claim 1 wherein the low pass filter is a fourth order Butterworth filter.

5. The method of claim 1 wherein the step of generating a beam of x-ray radiation onto the first planar surface is performed by an x-ray tube source.

6. The method of claim 1 wherein the step of measuring intensity of the beam of x-ray radiation below the second planar surface after is passes through the LVL billet is performed by a linear array detector.

7. The method of claim 1 wherein processing the measured intensity to create an image, the image comprising a plurality of pixels arranged in one or more columns includes creating an image having 128 pixels arranged in 128 columns.

* * * * *